United States Patent [19]

Nelson

[11] 4,010,192

[45] Mar. 1, 1977

[54] 5-OXA PHENYL- AND PHENOXY-SUBSTITUTED PROSTAGLANDIN $E_1$ ANALOGS

[75] Inventor: Norman A. Nelson, Galesburg, Mich.

[73] Assignee: The Upjohn Company, Kalamazoo, Mich.

[22] Filed: Feb. 23, 1976

[21] Appl. No.: 660,214

Related U.S. Application Data

[60] Continuation of Ser. No. 524,952, Nov. 18, 1974, abandoned, which is a division of Ser. No. 361,990, May 21, 1973, Pat. No. 3,864,387.

[52] U.S. Cl. .......................................... 260/473 G
[51] Int. Cl.² ......................................... C07C 69/76
[58] Field of Search ............................... 260/473 G

[56] References Cited

UNITED STATES PATENTS 3,980,694  9/1976  Bundy ........................... 260/473 G

*Primary Examiner*—Paul J. Killos
*Attorney, Agent, or Firm*—Morris L. Nielsen

[57] ABSTRACT

5-Oxa phenyl- and phenoxy-substituted prostaglandin-type compounds and processes for making them. These compounds are useful for a variety of pharmacological purposes, including anti-ulcer, inhibition of platelet aggregation, increase of nasal patency, labor inducement at term, and wound healing.

17 Claims, No Drawings

5-OXA PHENYL- AND PHENOXY-SUBSTITUTED PROSTAGLANDIN E₁ ANALOGS

CROSS REFERENCE TO RELATED APPLICATIONS

This is a continuation, of application Ser. No. 524,952, filed Nov. 18, 1974, now abandoned, which is a divisional of my co-pending application Ser. No. 361,990 filed May 21, 1973 new issued as U.S. Pat. No. 3,864,387.

BACKGROUND OF THE INVENTION

This invention relates to novel compositions of matter, to novel methods for producing those, and to novel chemical intermediates useful in those processes. Particularly, this invention relates to certain novel analogs of prostaglandins $E_1$, $F_{1\alpha}$, $F_{1\beta}$, $A_1$, and $B_1$ in which the C-5 methylene (—CH₂) in the prostanoic acid structure is replaced by oxygen (—O—).

The essential material for this application, including the background of the invention, the disclosure of the invention, and the description of the preferred embodiments, including Preparations and Examples, is incorporated by reference from U.S. Pat. No. 3,864,387, columns 1–89 inclusive, under the provisions of M.P.E.P. 608.01(p).

SUMMARY OF THE INVENTION

It is a purpose of this invention to provide novel 5-oxa prostagalandin E, F, A, and B analogs. It is a further purpose to provide novel 5oxa prostaglandin analogs with a variety of substituents and degrees of saturation in the side chains. It is a further purpose to provide 5-oxa prostaglandin anaglogs having the 11-deoxy ring-structure in which the 11-hydroxy is replaced by hydrogen. It is a further purpose to provide esters, lower alkanoates, and pharmacologically acceptable salts of said analogs. It is a further purpose to provide novel processes for preparing said analogs and esters. It is still a further purpose to provide novel intermediates useful in said processes.

The novel prostaglandin analogs of this invention each have an oxygen (—O—) in place of the methylene (—CH₂—) moiety at the 5-position of the prostanoic acid formula. They are represented by the generic formula

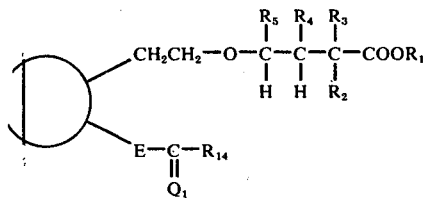

wherein D is one of the six carbocyclic moieties:

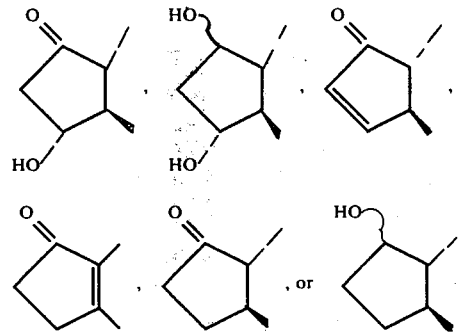

wherein ~ indicates alpha or beta attachment of hydroxyl to the cyclopentane ring; wherein E is —CH₂Ch₂— or

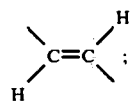

wherein $Q_1$ is

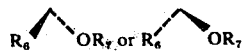

wherein $R_6$ and $R_7$ are hydrogen or alkyl of one of 4 carbon atoms, inclusive, being the same or different; wherein $R_1$ is hydrogen, alkyl of one 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; wherein $R_4$ and $R_5$ are hydrogen or alkyl of one to 4 carbon atoms, inclusive, being the same or different with the proviso that no more than one of $R_3$ $R_4$, and $R_5$ is alkyl; and wherein $R_{14}$ is

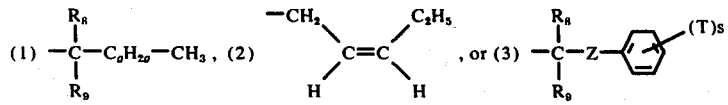

with the proviso that $R_{14}$ is

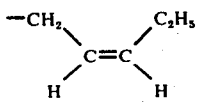

only when E is

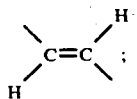

wherein $C_nH_{2n}$ is alkylene of one to 9 carbon atoms, inclusive, with one to 5 carbon atoms, inclusive, in the chain between —$CR_8R_9$— and terminal methyl; wherein $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro; wherein T is alkyl of one to 4 carbon atoms, inclusive, fluoro, chloro, trifluoromethyl, or —$OR_{10}$, wherein: $R_{10}$ is hydrogen or alkyl of one to 4 carbon atoms, inclusive, and s is zero, one, 2, or 3, with the proviso that not more than two T's are other than alkyl; and wherein Z represents an oxa atom (—O—) or $C_jH_{2j}$, wherein $C_jH_{2j}$ is a valence bond or alkylene of one to 9 carbon atoms, inclusive, substituted with zero, one, or 2 fluoro, with one to 6 carbon atoms, inclusive, between —$CR_8R_9$— and the ring.

The presently described acids and esters of the 5-oxa prostaglandin analogs include compounds of the following formulas which are intended to represent the same optically form as of the naturally occurring prostaglandins. There are also included the racemic compounds represented by each respective formula and the mirror image thereof. There are also included the alkanoates of two to 8 carbon atoms, inclusive and also the pharmacologically acceptable salts thereof when $R_1$ is hydrogen.

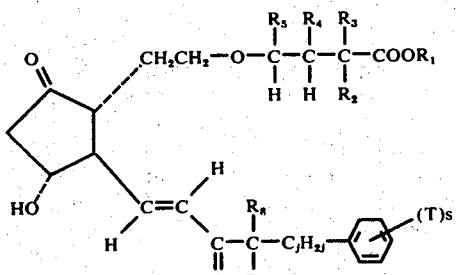

XXXIX

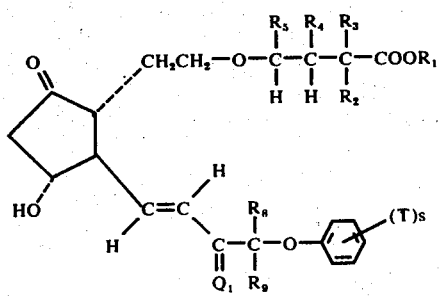

XLIII

I claim:
1. An optically active compound of the formula

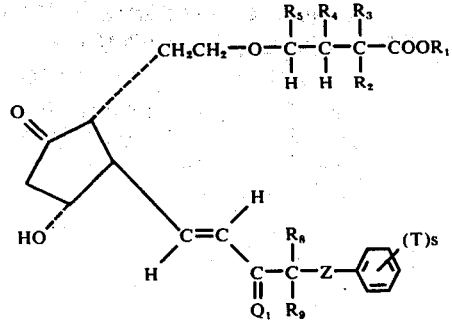

or a racemic compound of that formula and the mirror image thereof, wherein Z represents an oxa atom (—O— or $C_jH_{2j}$ wherein $C_jH_{2j}$ is a valence bond or alkylene of one to 9 carbon atoms, inclusive, substituted with zero, one, or 2 fluoro, with one to 6 carbon atoms, inclusive, between —$CR_8R_9$— and the ring; wherein T is alkyl of one to 4 carbon atoms, inclusive, fluoro, chloro, trifluoromethyl, or —$OR_{10}$, wherein $R_{10}$ is hydrogen or alkyl of one to 4 carbon atoms, inclusive, and s is zero, one, 2, or 3, with the proviso that not more than two T's are other than alkyl and when s is 2 or 3 the T's are either the same or different; wherein $Q_1$ is

wherein $R_6$ and $R_7$ are hydrogen or alkyl of one to 4 carbon atoms, inclusive, being the same or different; wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, or phenyl substituted with one, 2, or 3 chloro or alkyl of one to 4 carbon atoms, inclusive; wherein when Z is oxa (—O—), $R_8$ and $R_9$ are hydrogen or alkyl of one to 4 carbon atoms, being the same or different, and, when Z is $C_jH_{2j}$, $R_8$ and $R_9$ are hydrogen, alkyl of one to 4 carbon atoms, inclusive, or fluoro, being the same or different, with the proviso that $R_9$ is fluoro only when $R_8$ is hydrogen or fluoro; wherein $R_3$ is hydrogen, alkyl of one to 4 carbon atoms, inclusive, or fluoro; wherein $R_2$ is hydrogen or fluoro, with the proviso that $R_2$ is fluoro only when $R_3$ is hydrogen or fluoro; and wherein $R_4$ and $R_5$ are hydrogen or alkyl of one to 4 carbon atoms, inclusive, being the same or different, with the proviso that no more than one of $R_3$, $R_4$, and $R_5$ is alkyl; including the lower alkanoates thereof, and the pharmacologically acceptable salts thereof when $R_1$ is hydrogen.

2. A compound according to claim 1 wherein $Q_1$ is

wherein $R_6$ and $R_7$ are hydrogen or alkyl of one to 4 carbon atoms, inclusive, being the same or different.

3. A compound according to claim 2 wherein the sum of the carbon atoms in $R_6$, $R_7$, $R_8$, and $R_9$ taken together is not greater than 7.

4. A compound according to claim 3 wherein $R_3$, $R_4$, and $R_5$ are either hydrogen or methyl, and at least one of $R_3$, $R_4$, and $R_5$ is methyl.

5. A compound according to claim 3 wherein $R_2$, $R_3$, $R_4$, and $R_5$ are hydrogen.

6. A compound according to claim 5 wherein $R_6$, $R_7$, $R_8$, and $R_9$ are either hydrogen or methyl, and at least one of $R_6$, $R_7$, $R_8$, and $R_9$ is methyl.

7. A compound according to claim 6 wherein $R_6$ is methyl.

8. A compound according to claim 6 wherein $R_7$ is methyl.

9. A compound according to claim 6 wherein one or both of $R_8$ and $R_9$ are methyl.

10. A compound according to claim 5 wherein $R_6$, $R_7$, $R_8$, and $R_9$ are hydrogen.

11. A compound according to claim 10 wherein Z is oxo (—O—).

12. 5-Oxa-16-phenoxy-17,18,19,20-tetranor-$PGE_1$, methyl ester, a compound according to claim 11.

13. A compound according to claim 10 wherein Z is methylene.

14. An optically active compound according to claim 13.

15. A compound according to claim 14 wherein $R_1$ is alkyl of one to 12 carbon atoms, inclusive.

16. 5-Oxa-17-phenyl-18,19,20-trinor-$PGE_1$, methyl ester, a compound according to claim 15.

17. A compound according to claim 14 wherein $R_1$ is hydrogen.

* * * * *